United States Patent [19]

Enomoto et al.

[11] Patent Number: 5,472,974
[45] Date of Patent: Dec. 5, 1995

[54] BENZIMIDAZOLE DERIVATIVES, AGRICULTURAL AND HORTICULTURAL FUNGICIDES CONTAINING THE SAME AS AN ACTIVE INGREDIENT AND INTERMEDIATE COMPOUNDS THEREOF

[75] Inventors: Masayuki Enomoto, Takarazuka; Junya Takahashi, Hyogo; Tomoyuki Kusaba, Toyonaka; Masayo Sugano, Kyoto; Rei Matsunaga, Takarazuka; Masahiro Tamaki, Toyonaka, all of Japan

[73] Assignee: Sumitomo Chemical Company, Limited, Osaka, Japan

[21] Appl. No.: 175,763

[22] Filed: Dec. 30, 1993

Related U.S. Application Data

[62] Division of Ser. No. 894,007, Jun. 2, 1992, Pat. No. 5,310,747.

[30] Foreign Application Priority Data

Feb. 26, 1992 [JP] Japan .................. 4-039302

[51] Int. Cl.⁶ .................. A01N 43/90; C07D 491/044
[52] U.S. Cl. .................. 514/395; 514/228.2; 514/234.5; 544/581; 544/139; 548/302.1
[58] Field of Search .................. 544/58.1, 139; 548/302.1; 514/228.2, 234.5, 395

[56] References Cited

U.S. PATENT DOCUMENTS

| | | | |
|---|---|---|---|
| 3,501,492 | 3/1970 | Floyd | 548/332 |
| 3,576,818 | 4/1971 | Samuel et al. | 548/331 |
| 4,310,540 | 1/1982 | Lantzsch et al. | 514/465 |
| 4,536,502 | 8/1985 | Giraudon et al. | 514/227 |
| 4,560,693 | 2/1985 | Rainer | 514/338 |
| 4,611,003 | 9/1986 | Marhold et al. | 514/452 |
| 4,730,062 | 3/1988 | Seelye et al. | 549/462 |
| 4,767,444 | 8/1988 | Heywang et al. | 71/92 |
| 5,310,747 | 5/1994 | Enomoto et al. | 514/395 |

FOREIGN PATENT DOCUMENTS

| | | |
|---|---|---|
| 49012 | 5/1986 | Australia . |
| 688690 | 8/1987 | Australia . |
| 1136142 | 11/1982 | Canada . |
| 0219192 | 4/1987 | European Pat. Off. . |
| 0310558 | 4/1989 | European Pat. Off. . |
| 0487286 | 5/1992 | European Pat. Off. . |
| 2601010 | 1/1988 | France . |
| 62-198678 | 9/1987 | Japan . |
| 62-240666 | 10/1987 | Japan . |
| 63-5081 | 1/1988 | Japan . |
| 63-5061 | 1/1988 | Japan . |
| 63-211270 | 9/1988 | Japan . |

*Primary Examiner*—Patricia L. Morris
*Attorney, Agent, or Firm*—Stevens, Davis, Miller & Mosher

[57] ABSTRACT

A benzimidazole derivative having the formula,

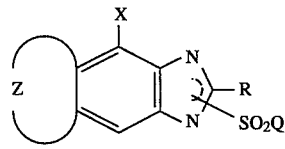

wherein R is cyano or thiocarbamoyl; Q is lower alkyl or a group represented by the formula $NQ^1Q^2$, in which $Q^1$ and $Q^2$ are independently lower alkyl, lower alkyl substituted with phenyl, lower alkenyl or lower alkynyl, or they form a lower alkylene ring when taken together at their ends which ring may include a hereto atom; X is hydrogen or halogen; and Z is a group which consists of (a) one oxygen atom or two non-adjacent oxygen atom, (b) —$CF_2$— group and (c) any one of a single bond, —$CF_2$—, —CFH—, CFCl— and —$CH_2$— groups and forms a five-membered or six membered ring together with two adjacent carbon atoms of the benzene ring; is obtained by reacting a corresponding 2-cyanobenzimidazole compound and a sulfamoyl chloride derivative. The benzimidazole derivative is incorporated into agricultural and horticultural fungicides as an active ingredient.

6 Claims, No Drawings

BENZIMIDAZOLE DERIVATIVES, AGRICULTURAL AND HORTICULTURAL FUNGICIDES CONTAINING THE SAME AS AN ACTIVE INGREDIENT AND INTERMEDIATE COMPOUNDS THEREOF

This is a division of application Ser. No. 07/894,007, filed Jun. 2, 1992, now U.S. Pat. No. 5,310,747.

The present invention relates to a benzimidazole derivative, a method for producing it, agricultural and horticultural fungicides containing it as an active ingredient and intermediates for producing it.

Captan, captafol and dithiocarbamate pesticides are known among those which are now widely used as an active ingredient for agricultural and horticultural fungicides, particularly as controlling agents for diseases such as late blight and downy mildew. These pesticides, however, may not always be said to be satisfactory as an active ingredient for agricultural and horticultural fungicides in terms of efficiency and the like.

In view of such situation, the present inventors have extensively studied to develop a compound having excellent efficacy against plant diseases and also giving little phytotoxicity. As a result they have found that the benzimidazole derivative of the present invention has excellent preventive and curative efficacy against plant diseases, is excellent in the systemic activity and further gives no phytotoxicity which would become a problem to crops. The present inventors thus attained to the present invention.

According to the present invention, there are provided a benzimidazole derivative having the formula (I) (hereinafter referred to as present compound),

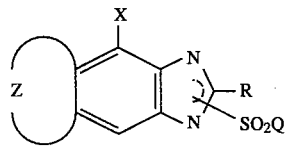
(I)

wherein R is cyano or thiocarbamoyl; Q is lower alkyl or a group represented by the formula, $NQ^1Q^2$, in which $Q^1$ and $Q^2$ are independently lower alkyl, lower alkyl substituted with phenyl, lower alkenyl or lower alkynyl, or they form a lower alkylene ring when taken together at their ends which ring may include a hetero atom; X is hydrogen or halogen; and Z is a group which consists of (a) one oxygen atom or two non-adjacent oxygen atoms, (b) —$CF_2$— group and (c) any one of a single bond, —$CF_2$—, —CFH—, —CFCl— and —$CH_2$— groups and forms a five-membered or six-membered ring together with the two adjacent carbon atoms of the benzene ring; a method for producing it; agricultural and horticultural fungicides containing it as an active ingredient and intermediates for producing it.

In the formula (I), the lower alkyl group represented by $Q^1$, $Q^2$ or Q includes $C_1$–$C_4$ alkyl groups such as methyl, ethyl, propyl, isopropyl, butyl, etc.; the lower alkenyl group represented by $Q^1$ or $Q^2$ includes $C_3$–$C_5$ alkenyl groups such as allyl, homoallyl, metaallyl, etc.; the lower alkynyl group represented by $Q^1$ or $Q^2$ includes $C_3$–$C_5$ alkynyl groups such as propargyl, etc.; the lower (usually $C_3$–$C_8$) alkylene ring, formed when $Q^1$ and $Q^2$ are taken together at their ends, which may include a hetero atom (e.g. oxygen atom, sulfur atom) includes butylene, pentylene, $CH_2CH_2OCH_2CH_2$, $CH_2CH_2SCH_2CH_2$, etc.; and the halogen atom represented by X includes fluorine, chlorine, bromine and iodine.

In the formula (I), Q is preferably dimethylamino. Z is preferably —$OCF_2O$—, —$CF_2CF_2O$—, $OCF_2CFHO$—, —$OCF_2CFClO$—, —$OCF_2CF_2O$—, —$OCF_2CH_2O$—, —$CF_2OCF_2$— or —$CF_2OCF_2O$—.

A method for producing the present compounds will be illustrated in detail.

Among the present compounds, the benzimidazole derivatives having the formula (I) in which R is cyano can be produced by reacting a 2-cyanobenzimidazole compound having the formula (II),

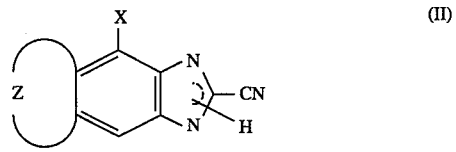
(II)

wherein X and Z are as defined above, with a sulfonyl chloride derivative having the formula (III),

$$Cl—SO_2Q \qquad (III)$$

wherein Q is as defined above.

In this reaction, the reaction temperature is usually in the range of from room temperature to the refluxing temperature of the solvent, and the reaction time is usually in the range of from a moment to about 24 hours.

This reaction is usually carried out in the presence of a base. Specific examples of the base used are tertiary amines (e.g. pyridine, triethylamine, N,N-dimethylaniline, tributylamine, N-methylmorpholine), inorganic bases (e.g. sodium hydroxide, potassium hydroxide, potassium carbonate) and the like.

Referring to the amounts of the reagents used for the reaction, the amount of the sulfonyl chloride derivative of the formula (III) is usually 1 to 3 moles per mole of the 2-cyanobenzimidazole compound of the formula (II), and that of the base is usually 1 to 7 moles per mole of the compound (II).

The above reaction is usually carried out in the presence of a solvent. Specific examples of the usable solvents are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate, diethyl carbonate), nitriles (e.g. acetonitrile, isobutyronitrile), amides (e.g. formamide, N,N-dimethylformamide), sulfur compounds (e.g. dimethyl sulfoxide) and the mixtures thereof.

After completion of the reaction, the reaction solution is subjected to usual after-treatments such as extraction with organic solvents, washing with water, concentration of the organic layer under reduced pressure, etc., and then the resulting product is purified if necessary by operations such as chromatography, recrystallization, etc. Thus, the desired present compound can be obtained.

Among the present compounds, the benzimidazole derivatives having the formula (I) in which R is thiocarbamoyl are obtained by reacting the 2-cyanobenzimidazole derivatives having the formula (I) in which R is cyano with hydrogen sulfide.

In this reaction, the reaction time is usually in the range of from a moment to 24 hours, and the reaction temperature is usually in the range of from 0° to 70° C. This reaction is usually carried out in the presence of a base. Specific examples of the base are organic bases such as pyridine, triethylamine, diethylamine, etc. Although a solvent is not always necessary in this reaction, it may be used if necessary. Specific examples of the usable solvent are ethers such as dioxane, tetrahydrofuran, etc.

Referring to the amounts of the reagents used for the reaction, the amount of each of hydrogen sulfide and the base is usually from 1 mole to a large excess per mole of the 2-cyanobenzimidazole derivative.

Among the 2-cyanobenzimidazole compounds having the formula (II), those having no $C_2$ symmetry axis exhibit tautomerism as shown in the formula (IV),

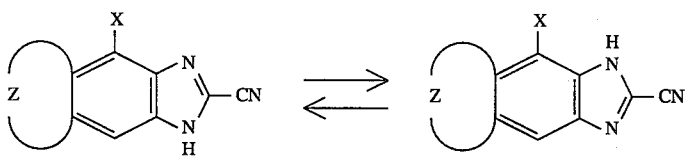

(IV)

wherein X and Z are as defined above. Therefore, production of the present compounds using those compounds by the above method gives either one of the compounds of the formulae (V) and (VI),

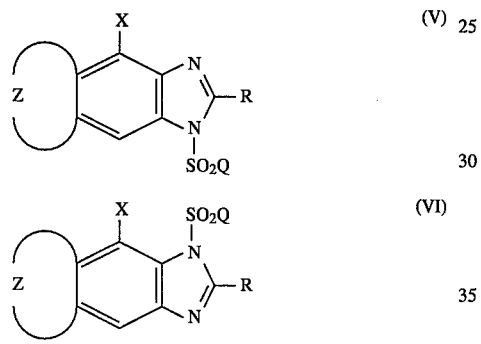

wherein R, Q, X and Z are as defined above, or a mixture of the both. Consequently, in the case where the 2-cyanobenzimidazole compounds having the formula (II) have no $C_2$ symmetry axis, the present compounds of the formula (I) derived therefrom are understood to refer to either one of the compounds having the formulae (V) and (VI) or the mixture thereof.

In the present compounds, when Z forms a five-membered ring together with two carbon atoms of the benzene ring, Z can be expressed as $—A_1—A_2—A_3—$. When $A_1—A_2—A_3$ and $A_3—A_2—A_1$ are not synonymous with each other (for example, as in the case where Z is $—CF_2CF_2O—$), the compounds having the formula (I) contain two isomers having the formulae (VII) and (VIII),

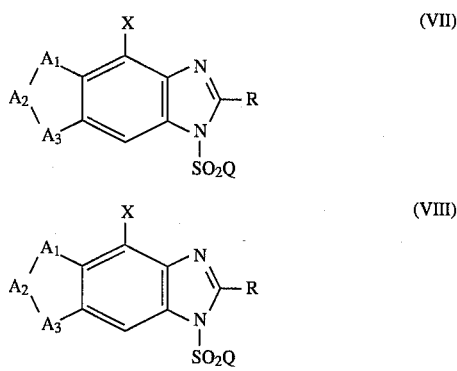

wherein X, R and Q are as defined above, and each of $A_1$, $A_2$ and $A_3$, which may be the same or different, represents one atom or atomic group satisfying the foregoing definition of Z, and $A_1—A_2—A_3$ and $A_3—A_2—A_1$ are different from each other. Those isomers each and their mixture are understood to also be included in the present compounds.

When Z forms a six-membered ring together with two carbon atoms of the benzene ring, Z can be expressed as $—B_1—B_2—B_3—B_4—$. When $B_1—B_2—B_3—B_4$ and $B_4—B_3—B_2—B_1$ are not synonymous with each other (for example, as in the case where Z is $—OCF_2CFHO—$), the compounds having the formula (I) contain two isomers having the formulae (IX) and (X),

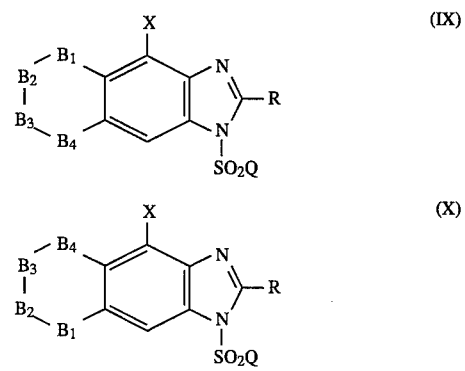

wherein X, R and Q are as defined above, and each of $B_1$, $B_2$, $B_3$ and $B_4$, which may be the same or different, represents one atom or atomic group satisfying the foregoing definition of Z, and $B_1—B_2—B_3—B_4$ and $B_4—B_3—B_2—B_1$ are different from each other. These isomers each and their mixture are understood to also be included in the present compounds.

The 2-cyanobenzimidazole compounds, a starting material for producing the present compounds, having the formula (II) is obtained by reacting a 2-(trichloromethyl)benzimidazole compound having the formula (XI),

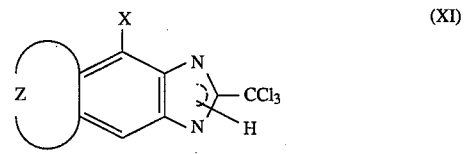

wherein X and Z are as defined above, with ammonia.

In this reaction, the reaction temperature is usually in the range of from −30° C. to the refluxing temperature of the solvent, and the reaction time is usually in the range of from a moment to about 24 hours.

Referring to the amount of the reagent used for the reaction, the amount of ammonia is usually from 6 moles to a large excess per mole of the 2-(trichloromethyl)benzimidazole compound having the formula (XI).

The above reaction is usually carried out in the presence of a solvent. Specific examples of the usable solvents are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate, diethyl carbonate), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), water and the mixtures thereof.

After completion of the reaction, the reaction solution is neutralized with an inorganic acid (e.g. hydrochloric acid) and then subjected to after-treatments such as extraction with organic solvents, washing with water, concentration of the organic layer, etc. Thus, the desired compound can be obtained.

The 2-(trichloromethyl)benzimidazole compound having the formula (XI) can be obtained by reacting an o-phenylenediamine compound having the formula (XII),

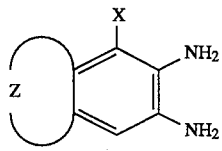

wherein X and Z are as defined above, with a trichloroacetoimidate compound having the formula (XIII),

wherein $R^1$ is lower alkyl.

In this reaction, the reaction temperature is usually in the range of from $-30°$ C. to the refluxing temperature of the solvent, and the reaction time is usually in the range of from a moment to about 24 hours.

Referring to the amount of the reagent used for the reaction, the amount of the trichloroacetoimidate compound having the formula (XIII) is usually 1 to 2 moles per mole of the o-phenylenediamine compound having the formula (XII).

The above reaction is usually carried out in the presence of a solvent. Specific examples of the usable solvent are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), organic acids (e.g. formic acid, acetic acid, propionic acid), and the mixtures thereof.

After completion of the reaction, the reaction solution is subjected, for example, to after-treatments such as pouring into ice water and separation of the resulting crystals by filtration, or extraction with organic solvents, washing with water, concentration, etc. The resulting product is then purified if necessary by operations such as chromatography, recrystallization, etc. Thus, the desired compound can be obtained.

The 2-(trichloromethyl)benzimidazole compound having the formula (XI) can also be obtained by reacting the o-phenylenediamine compound having the formula (XII) with trichloroacetyl chloride to obtain a 2-aminotrichloroacetoanilide compound and subjecting the 2-aminotrichloroacetoanilide compound to cyclization reaction.

In this cyclization reaction, the reaction temperature is usually in the range of from $40°$ C. to the refluxing temperature of the solvent, and the reaction time is usually in the range of from a moment to about 24 hours.

The above reaction is usually carried out in the presence of a solvent. Specific examples of the solvents usable for the reaction are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate, diethyl carbonate), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), water and the mixtures thereof.

The reaction of the o-phenylenediamine compound of the formula (XI) with trichloroacetyl chloride can be carried out in the same manner as in the reaction of the 2-cyanobenzimidazole compound of the formula (II) with the sulfonyl chloride compound of the formula (III).

The o-phenylenediamine derivative having the formula (XII) can be obtained by reducing an o-nitroaniline compound having the formula (XIV),

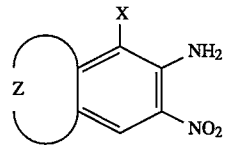

wherein X and Z are as defined above.

The reduction method which can be used includes, for example, a method of carrying out reduction using sodium sulfide or sodium hydrogensulfide in a mixture of water and a lower alcohol such as methanol, ethanol, etc. The reaction temperature is usually in the range of from $50°$ C. to the refluxing temperature of the solvent, and the reaction time is usually within 12 hours.

Also, this reduction can be carried out by a method using iron powders, zinc powders or tin powders in a mixture of water and either an organic acid (e.g. acetic acid) or an inorganic acid (e.g. hydrochloric acid, sulfuric acid). This reaction is usually carried out at from $30°$ to $100°$ C. and within 12 hours.

Further, a method of carrying out hydrogenation in the temperature range of usually from $0°$ to $60°$ C. at normal pressure or under pressure using a catalyst (e.g. platinum dioxide, palladium-carbon) in an organic solvent (e.g. ethanol, ethyl acetate) can also be used.

The o-phenylenediamine compound having the formula (XII) can also be obtained by reducing an o-dinitro compound having the formula (XV),

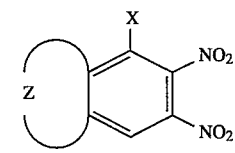

wherein X and Z are as defined above.

The reduction method includes, for example, a method described in JP-A-62-198678 and a method of carrying out hydrogenation in the temperature range of usually from $0°$ to $50°$ C. at normal pressure or under pressure in an organic solvent (e.g. ethanol, ethyl acetate) using a catalyst such as platinum dioxide, palladium-carbon and the like.

Some of the compounds having the formula (XV) are disclosed in JP-A-62-198678. The rest of the compounds having the formula (XV) can be prepared by the same method as described in JP-A-62-198678 starting from a 1,2-difluoromethylenedioxybenzene derivative, a fluorinated benz-1,4-dioxene derivative or the like.

The o-nitroaniline compound having the formula (XIV) is obtained by hydrolyzing an o-nitroanilide compound having the formula (XVI),

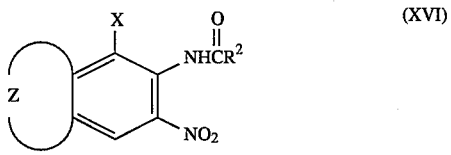

wherein X and Z are as defined above, and $R^2$ is lower alkyl.

The reaction temperature is usually in the range of from room temperature to 100° C. or the refluxing temperature of the solvent, and the reaction time is usually in the range of from a moment to about 24 hours.

The above reaction is usually carried out in the presence of a base or acid. Specific examples of the base are inorganic bases such as sodium hydroxide, potassium hydroxide, etc. Specific examples of the acid are inorganic acids such as hydrochloric acid, sulfuric acid, etc.

Referring to the amount of the reagent used for the reaction, the amount of the base or acid is from a catalytic amount to a large excess per mole of the o-nitroanilide compound having the formula (XVI).

The reaction is carried out with or without a solvent depending upon the kind of the base or acid used. Specific examples of the usable solvent are aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), nitriles (e.g. acetonitrile, isobutyronitrile), amides (e.g. formamide, N,N-dimethylformamide), sulfur compounds (e.g. dimethyl sulfoxide), alcohols (e.g. methanol, ethanol, 2-propanol), organic acids (formic acid, acetic acid, propionic acid), water and the mixtures thereof.

The o-nitroaniline compound of the formula (XIV) wherein X is chlorine or bromine can also be obtained by chlorinating or brominating a compound having the formula (XVII),

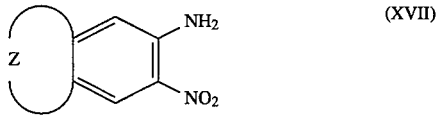

wherein Z is as defined above.

In this reaction, the reaction temperature is usually in the range of from 0° C. to the refluxing temperature of the solvent, and the reaction time is usually in the range of from a moment to about 24 hours.

Referring to the amount of the reagents used for the reaction, the amount of the chlorinating or brominating agent is from 1 mole to a large excess per mole of the compound having the formula (XVII).

Chlorine, N-chlorosuccinimide, sulfuryl chloride, etc. can be used as a chlorinating agent. Bromine, N-bromosuccinimide, etc. can be used as a brominating agent.

Specific examples of the solvent usable for this reaction are halogenated hydrocarbons (e.g. chloroform, carbon tetrachloride, dichloroethane), ethers (e.g. diethyl ether, dioxane, tetrahydrofuran), organic acids (e.g. formic acid, acetic acid, propionic acid), water and the mixtures thereof.

The o-nitroanilide compound having the formula (XVII) can be obtained by nitrating an anilide compound having the formula (XVIII),

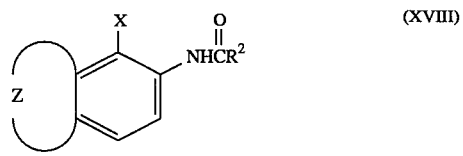

wherein X, Z and $R^2$ are as defined above.

In this reaction, the reaction temperature is usually from –40° C. to 20° C., and the reaction time is usually from a moment to 24 hours.

As the nitrating agent, fuming nitric acid, nitric acid, sodium nitrate and potassium nitrate can be used. As the solvent, acetic acid, acetic anhydride, sulfuric acid, fuming sulfuric acid, water and the mixtures thereof can be used.

Referring to the amount of the reagent used for the reaction, the amount of the nitrating agent is from 1 mole to a large excess per mole of the compound represented by the formula (XVIII).

Among the o-nitroanilide compounds having the formula (XVI), the compounds having the formula (XIX),

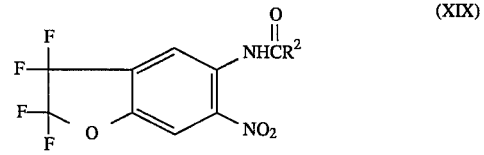

wherein $R^2$ is lower alkyl, can also be obtained by cyclization of a compound having the formula (XX),

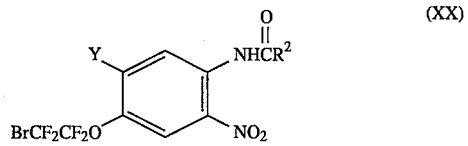

wherein Y is bromine or chlorine, and $R^2$ is lower alkyl, in the presence of metallic copper.

The reaction temperature is usually in the range of from 50° C. to the refluxing temperature of the solvent, and the reaction time is usually in the range of a moment to 24 hours.

The amount of copper used for the reaction is usually from 2 moles to a large excess per mole of the compound having the formula (XIX).

The above reaction is usually carried out in a solvent. Specific examples of the usable solvent are amides (e.g. formamide, N,N-dimethylformamide), sulfur compounds (e.g. dimethyl sulfoxide) and the mixtures thereof.

After completion of the reaction, the reaction solution is for example filtered and then subjected to after-treatments such as extraction of the filtrate with an organic solvent, washing with water, concentration, etc. The product obtained is purified if necessary by operations such as chromatography, recrystallization, etc. Thus, the desired compound can be obtained.

The anilide compound having the formula (XVIII) can be obtained by acylating an aniline compound having the formula (XXI),

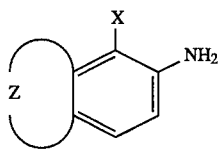

wherein X and Z are as defined above.

The reaction temperature is usually in the range of from room temperature to 120° C. or the refluxing temperature of the solvent, and the reaction time is usually in the range of from a moment to about 24 hours.

This reaction is usually carried out in the presence of a base or acid. Specific examples of the base used are tertiary amines (e.g. pyridine, triethylamine, N,N-dimethylaniline, tributylamine, N-methylmorpholine), inorganic bases (e.g. sodium hydroxide, potassium hydroxide, potassium carbonate) and the like. Specific examples of the acid are organic acids (e.g. formic acid, acetic acid, propionic acid) and inorganic acids (e.g. sulfuric acid).

The amount of the base or acid used for the reaction is from a catalytic amount to a large excess per mole of the aniline compound having the formula (XXI).

Specific examples of the acylating agent used in the above reaction are corresponding acid anhydrides, acid halides, ester compounds, carboxylic acids, etc.

The amount of the acylating agent used for the reaction is from 1 mole to a large excess per mole of the aniline compound having the formula (XXI).

The solvent used is determined depending upon the base or acid used. When the solvent is used, it includes aliphatic hydrocarbons (e.g. hexane, petroleum ether), aromatic hydrocarbons (e.g. benzene, toluene), halogenated hydrocarbons (e.g. chloroform, dichloroethane), ethers (e.g. diethyl ether, dioxane, tetrahydrofuran), ketones (e.g. acetone, methyl ethyl ketone), esters (e.g. ethyl acetate), nitriles (e.g. acetonitrile, isobutyronitrile), amides (e.g. formamide, N,N-dimethylformamide), sulfur compounds (e.g. dimethylsulfoxide), organic acids (e.g. formic acid, acetic acid, propionic acid) and the mixtures thereof.

Among the compounds having the formula (XVIII), compounds having the formula (XXII),

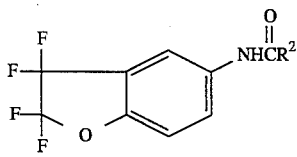

wherein $R^2$ represents a lower alkyl group, are obtained by cyclization of a compound having the formula (XXIII),

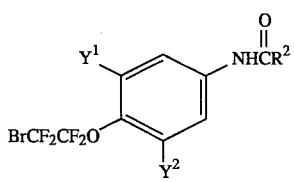

wherein $Y^1$ and $Y^2$ are independently hydrogen, bromine or chlorine provided that $Y^1$ and $Y^2$ are not a hydrogen atom at the same time, and $R^2$ is lower alkyl, with metallic copper.

This cyclization reaction can be carried out in the same manner as in the cyclization of the compound having the formula (XX).

The aniline compound having the formula (XXI) is disclosed or can be produced by the methods described, for example, in Liebigs Ann. Chem., 730, 16–30 (1969), and JP-A-55-69576, U.S. Pat. No. 4,767,779, Chemical Abstracts, 60, 13352h etc.

Other than the method described above, the o-nitroaniline compound having the formula (XVII) can also be prepared by reacting a compound having the formula (XXIII),

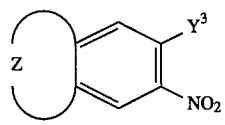

wherein Z is as defined above, $Y^3$ is nitro or halogen, with ammonia.

In this reaction, the reaction temperature usually within the range of from 0° C. to the refluxing temperature of the solvent, and the reaction time is usually within the range of from a moment to about 24 hours.

Referring to the amount of the reagents used for the reaction, the amount of ammonia is from 1 mole to a large excess per mole of the compound having the formula (XXIII).

Specific examples of the solvent usable for this reaction are aliphatic hydrocarbons (e.g. hexane, petroleum ether), aromatic hydrocarbons (e.g. benzene, toluene), ethers (e.g. diethylether, dioxane, tetrahydrofuran), amides (e.g. formamide, N,N-dimethylformamide), sulfur compounds (e.g. dimethyl sulfoxide), alcohols (e.g. methanol, ethanol, 2-propanol), water and the mixtures thereof.

Some of the compounds having the formula (XXIII) are disclosed in Chemical Abstracts, 60, 13353c (1964) or in JP-A-62-198678. The rest of the compounds having the formula (XXIII) can be prepared by the same method as described in JP-A-62-198678 starting from 1,2-difluoromethylenedioxybenzene or the like.

The present compound itself may be used as an active ingredient for agricultural and horticultural fungicides without adding any other ingredients. Usually, however, it is formulated into emulsifiable concentrates, wettable powders, suspension formulations, dusts, granules, dry flowable formulations, etc. by mixing with solid carriers, liquid carriers, gaseous carriers, surface active agents and other auxiliaries for formulation. In this case, the content of the present compound, which is an active ingredient, in the formulations is usually from 0.01 to 99%, preferably from 0.1 to 80%.

Specific examples of the solid carriers are fine powders or granules of clays (e.g. kaolin clay, diatomaceous earth, synthetic hydrated silicon dioxide, Fubasami clay, bentonite, terra alba), talcs, other inorganic minerals (e.g. sericite, calcite powder, quartz powder, activated carbon, calcium carbonate, hydrated silica), chemical fertilizers (e.g. ammonium sulfate, ammonium phosphate, ammonium nitrate, urea, ammonium chloride), corn stalk powder, walnut shell powder, etc. Specific examples of the liquid carriers are water, alcohols (e.g. methanol, ethanol, ethylene glycol, cellosolve), ketones (e.g. acetone, methyl ethyl ketone, isophorone), aromatic hydrocarbons (e.g. benzene, toluene, xylene, ethylbenzene, methylnaphthalene), aliphatic hydrocarbons (e.g. n-hexane, cyclohexane, kerosene, gas oil), esters (e.g. ethyl acetate, butyl acetate), nitriles (e.g. acetonitrile, isobutyronitrile), ethers (e.g. dioxane, diisopropyl ether), acid amides (e.g. dimethylformamide, dimethylacetamide), halogenated hydrocarbons (e.g. dichloroethane, trichloroethylene, carbon tetrachloride), vegetable oils (e.g.

soybean oil, cotton seed oil), dimethyl sulfoxide, etc. Specific examples of the gaseous carriers, i.e. a propellant, are freon gas (registered trade name), butane gas, carbon dioxide gas, etc.

Specific examples of the surface active agents are anionic surface active agents such as alkyl sulfates, alkylaryl esters, alkylsulfonates, alkylarylsulfonates, dialkyl sulfosuccinates, the salts of a polyoxyethylene alkylaryl ether phosphoric acid ester, naphthalenesulfonic acid/formalin condensates, etc. and nonionic surface active agents such as polyoxyethylene alkyl ethers, polyoxyethylene polyoxypropylene block copolymers, sorbitan fatty acid esters, polyhydric alcohol esters, sugar alcohol derivatives, etc.

Specific examples of the fixing agents and dispersing agents are casein, gelatin, polysaccharides [e.g. starch powder, gum arabic, cellulose derivatives {e.g. CMC (carboxymethyl cellulose)}, lignin derivatives {e.g. lignosulfonate}, alginic acid], bentonite, synthetic water-soluble high polymers (e.g. polyvinyl alcohol, polyvinyl pyrrolidone, polyacrylic acids), etc. Specific examples of the stabilizing agents are PAP (isopropyl acid phosphate), BHT (2,6-di-tert-butyl-4-methylphenol), BHA (a mixture of 2-tert-butyl-4-methoxyphenol and 3-tert-butyl- 4-methoxyphenol), vegetable oils, mineral oils, surface active agents, fatty acids and their esters, etc.

The application methods for the present compound are foliar application, soil treatment, seed disinfection and the like. However, any application method which is commonly used by the skilled artisan may be used.

When the present compound is used as an active ingredient for agricultural and horticultural fungicides, the dosage rate of the active ingredient varies with target crops, target diseases, degrees of outbreak of diseases, preparation forms, application methods, application times, weather conditions, etc. Usually, however, the dosage rate is 0.01 to 50 g/are, preferably 0.05 to 10 g/are. When the emulsifiable concentrates, wettable powders, suspension formulations, dry flowable concentrates, etc. are applied diluted with water, the application concentration of the active ingredient is 0.0001 to 0.5%, preferably 0.0005 to 0.2%. The dusts, granules, etc. are applied as they are without being diluted.

As plant diseases which can be controlled with the present compound, for example, the following ones can be given.

Downy mildew of vegetables and Japanese radish (*Peronospora brassicae*), downy mildew of spinach (*Peronospora spinaciae*), downy mildew of tobacco (*Peronospora tabacina*), downy mildew of cucumber (*Pseudoperonospora cubensis*), downy mildew of grape (*Plasmopara viticola*), late blight of apple, strawberry and ginseng (*Phytophthora cactorum*), phytophthora rot of tomato and cucumber (*Phytophthora capsici*), late blight of pineapple (*Phytophthora cinnamomi*), late blight of potato, tomato and eggplant (*Phytophthora infestans*), late blight of tobacco, broad bean and Welsh onion (*Phytophthora nicotianae* var. *nicotianae*), damping-off of spinach (*Pythium* sp.), damping-off of cucumber (*Pythium aphanidermatum*), browning root rot of wheat (*Pythium* sp.), damping-off of tobacco (*Pythium debaryanum*) and Pythium rot of soybean (*Pythium aphanidermatum, P. debaryanum, P. irregulare, P. myriotylum, P. ultimum*).

The present compound can be used as agricultural and horticultural fungicides in plow fields, paddy fields, orchards, tea gardens, pastures, turfs, etc. It can also be used in mixture with other agricultural and horticultural fungicides. Further, it can also be used in mixture with insecticides, acaricides, nematocides, herbicides, plant growth regulators and fertilizers.

The present compounds have excellent preventive and curative effect particularly on various diseases caused by Phycomycetes. One or more of the present compounds can be mixed with at least one fungicidal active ingredient selected from the group consisting of chlorothalonil, fluazinam, dichlofluanide, phosethyl-aluminum, cyclic imide fungicides (e.g. captan, captafol, folpet), dithiocarbamate fungicides (e.g. maneb, mancozeb, thiram, ziram, zineb, propineb), inorganic or organic copper fungicides (e.g. basic cupric sulfate, basic cupric chloride, cupric hydroxide, oxine-copper), cymoxanil, acylalanine fungicides (e.g. metalaxyl, furalaxyl, ofurace, cyprofuram, benalaxyl, oxadixyl) and compounds disclosed in JP-A-1-301681 (e.g. N-[cyano(2'-furyl)methyl]-2,4-dimethylthiazole- 5-carboxyamide, N-[cyano(3'-furyl)methyl]- 2,4-dimethylthiazole-5-carboxyamide, N-[cyano(2 '-thienyl)methyl]- 2,4-dimethylthiazole-5-carboxyamide, N-[cyano(3-thienyl)methyl]-2,4-dimethylthiazole- 5-carboxyamide, N-[cyano(2'-furyl)methyl]-2-methyl- 4-ethylthiazole-5-carboxyamide, N-[cyano(3'-furyl)methyl]-2-methyl- 4-ethylthiazole-5-carboxyamide, N-[cyano(2 '-thienyl)methyl]-2-methyl-4-ethylthiazole- 5-carboxyamide and N-[cyano(3'-thienyl)methyl]-2-methyl- 4-ethylthiazole-5-carboxyamide. The resulting mixture can be used as a fungicide in the same manner for the present compounds as described above. Hereupon, the mixing ratios of the present compound(s) to chlorothalonil, fluazinam, dichlofluanide, phosethyl-aluminum, cyclic imide fungicides, dithiocarbamate fungicides or the inorganic or organic copper fungicides are usually within the range of from 1:1 to 1:200 in terms of the weight of the active ingredient. The mixing ratios of the present compound(s) to cymoxanil, the acylalanine fungicides or compounds disclosed in JP-A-1-301681 are usually within the range of from 1:0.1 to 1:20 in terms of the weight of the active ingredient. In this case, these active ingredients can be used by mixing them and then formulating as described above, or by formulating each of them as described above and then mixing. Use of the present compound(s) in mixture with other fungicide(s) as above is expected to synergistically improve the efficacy particularly on various diseases caused by Phycomycetes.

The present invention will be illustrated in more detail with reference to the following production examples, formulation examples and test examples. However, the present invention is not to be interpreted as being limited thereto.

Production Example 1

2.83 Grams of a 2-cyanobenzimidazole compound [compound (i)] of the formula (II) in which X is H and Z is OCF$_2$CFHO was dissolved in 50 ml of acetonitrile. 3.8 Grams of potassium carbonate was added thereto. The resulting mixture was heated under reflux for 15 minutes. Thereafter, 2.6 g of dimethylsulfamoyl chloride was added to the refluxed mixture. Refluxing was continued for additional 40 minutes with heating. The reaction solution was poured into ice water and extracted with ethyl acetate. The organic layer was washed with water and dried over anhydrous sodium sulfate. A residue was obtained by removing the solvent from the dried layer by distillation. Column chromatographying the residue on silica gel with toluene as an eluent gave 1.53 g of a benzimidazole derivative [present compound (1)] of the formula (I) in which X is H, Z is OCF$_2$CFHO, R is CN and Q is N(CH$_3$)$_2$.

Production Example 2

0.95 Gram of the present compound (1) was dissolved in 20 ml of pyridine. The resulting solution was stirred for 1 hour and 45 minutes in a hydrogen sulfide atmosphere. After reaction, the reaction solution was extracted with ethyl acetate. The organic layer was washed with water and dried over anhydrous sodium sulfate. Crystals were obtained by removing the solvent from the dried layer by distillation. Column chromatographying the crystals on silica gel with a chloroform/ethyl acetate mixed solution as an eluent and recrystallizing them from hexane/ethyl acetate gave 0.83 g of a benzimidazole derivative [present compound (4)] of the formula (I) in which X is H, Z is $OCF_2CFHO$, R is thiocarbamoyl and Q is $N(CH_3)_2$.

Production Example 3

1.8 Grams of a 2-cyanobenzimidazole compound [compound (iii)] of the formula (II) in which X is Br and Z is $OCF_2CFHO$ was dissolved in 70 ml of acetonitrile. 1.5 Grams of potassium carbonate was added thereto. The resulting mixture was heated under reflux for 20 minutes. Thereafter, 1.2 g of dimethylsulfamoyl chloride was added thereto. Refluxing was continued for 1 hour with heating. The reaction solution was poured into ice water and extracted with ethyl acetate. The organic layer was washed with water, dried over anhydrous sodium sulfate and concentrated. Column chromatographying the resulting residue on silica gel with chloroform as an eluent and recrystallizing it from hexane/ethyl acetate gave 1.18 g of a benzimidazole derivative [present compound (3)] of the formula (I) in which X is Br, Z is $OCF_2CFHO$, R is CN and Q is $N(CH_3)_2$.

Production Example 4

1.5 Grams of a 2-cyanobenzimidazole compound [compound (ii)] of the formula (II) in which X is F and Z is $OCF_2CFHO$ was dissolved in 50 ml of acetonitrile. 2.0 Grams of potassium carbonate was added thereto. The resulting mixture was heated under reflux for 25 minutes. Thereafter, 1.5 g of dimethylsulfamoyl chloride was added thereto. Refluxing was continued for 40 minutes with heating. The reaction solution was poured into ice water and extracted with ethyl acetate. The organic layer was washed with water, dried over anhydrous sodium sulfate and concentrated. Column chromatographying the resulting residue on silica gel with toluene as an eluent and recrystallizing it from hexane/ethyl acetate gave 0.9 g of a benzimidazole derivative [present compound (2)] of the formula (I) in which X is F, Z is $OCF_2CFHO$, R is CN and Q is $N(CH_3)_2$ (bubble-form compound).

Production Example 5

6.2 Grams of a 2-cyanobenzimidazole compound [compound (iv)] of the formula (II) in which X is H and Z is $OCF_2O$ was dissolved in 100 ml of acetonitrile. 10 Grams of potassium carbonate was added thereto. The resulting mixture was heated under reflux for 15 minutes. Thereafter, 6.7 g of dimethylsulfamoyl chloride was added thereto. Refluxing was continued for 15 minutes with heating. The reaction solution was poured into ice water and extracted with ethyl acetate. The organic layer was washed with water and dried over anhydrous sodium sulfate. Crystals were obtained by removing the solvent from the dried layer by distillation. Recrystallizing the crystals from hexane/ethyl acetate and then from chloroform/methanol gave 2.4 g of benzimidazole derivative [present compound (15)] of the formula (I) in which X is H, Z is $OCF_2O$, R is CN and Q is $N(CH_3)_2$.

Production Example 6

0.4 Gram of the present compound (15) was dissolved in 10 ml of pyridine and reacted for 2 hours and 30 minutes in a hydrogen sulfide atmosphere. After reaction, the reaction solution was distributed between ethyl acetate and water. The organic layer was washed with water and dried over anhydrous sodium sulfate. Crystals were obtained by removing the solvent by distillation. Recrystallizing the crystals from hexane/ethyl acetate gave 0.24 g of a benzimidazole derivative present compound (18)] of the formula (I) in which X is H, Z is $OCF_2O$, R is thiocarbamoyl and Q is $N(CH_3)_2$.

Production Example 7

1.5 Grams of a 2-cyanobenzimidazole compound [compound (vi)] of the formula (II) in which X is Br and Z is $OCF_2O$ was dissolved in 60 ml of acetonitrile. 2.0 Grams of potassium carbonate was added thereto. The resulting mixture was heated under reflux for 15 minutes. Thereafter, 2.0 g of dimethylsulfamoyl chloride was added thereto. Refluxing was continued for 15 minutes with heating. The reaction solution was poured into ice water and extracted with ethyl acetate. The organic layer was washed with water, dried over anhydrous sodium sulfate and concentrated. Column chromatographying the resulting residue on silica gel with chloroform as an eluent and recrystallizing it from hexane/ethyl acetate gave 1.3 g of benzimidazole derivative [present compound (17)] of the formula (I) in which X is Br, Z is $OCF_2O$, R is CN and Q is $N(CH_3)_2$.

The benzimidazole derivative obtained above was further recrystallized from toluene. X-ray analysis of the recrystallized benzimidazole demonstrated that it was one of the regio isomers and contained the $SO_2N(CH_3)_2$ group attached to one of the nitrogen atoms constituting the benzimidazole ring furthest from the bromine atom.

Production Example 8

2.05 Grams of a 2-cyanobenzimidazole compound of the formula (II) in which X is F and Z is $OCF_2O$ was dissolved in 50 ml of acetonitrile. 2.0 Grams of potassium carbonate was added thereto. The resulting mixture was heated under reflux for 20 minutes. Thereafter, 1.3 g of dimethylsulfamoyl chloride was added thereto. Refluxing was continued for 45 minutes with heating. The reaction solution was poured into ice water and extracted with ethyl acetate. The organic layer was washed with water, dried over anhydrous sodium sulfate and concentrated. Column chromatographying the resulting residue on silica gel with chloroform as an eluent and recrystallizing it from hexane/ethyl acetate gave 1.33 g of benzimidazole derivative [present compound (16)] of the formula (I) in which X is F, Z is $OCF_2O$, R is CN and Q is $N(CH_3)_2$.

Production Example 9

0.6 Gram of a 2-cyanobenzimidazole compound of the formula (II) in which X is H and Z is $CF_2CF_2O$ was dissolved in 30 ml of acetonitrile. 0.75 Gram of potassium carbonate was added thereto. The resulting mixture was heated under reflux for 20 minutes. Thereafter, 0.4 g of dimethylsulfamoyl chloride was added thereto. Refluxing was continued for 1 hour with heating. The reaction solution was poured into ice water and extracted with ethyl acetate. The organic layer was washed with water and dried over anhydrous sodium sulfate. A residue was obtained by removing the solvent from the dried layer by distillation. Column chromatographying the residue on silica gel with toluene as an eluent gave 0.23 g of a benzimidazole derivative [present compound (29)] of the formula (I) in which X is H, Z is $CF_2CF_2O$, R is CN and Q is $N(CH_3)_2$. $^1$H-NMR spectrum showed that the product was a mixture of two regio isomers.

Examples of the present compound which can be produced by the above methods will be shown in Tables 1 to 9.

TABLE 1

Benzimidazole derivatives having the formula (I):

| Compound No. | X | Z | R | Q | Melting point (°C.) | $^1$H-NMR (Internal standard: TMS) Solvent: δ (ppm) |
| --- | --- | --- | --- | --- | --- | --- |
| (1) | H | OCF$_2$CFHO | CN | N(CH$_3$)$_2$ | 115–118 | CDCl$_3$; 7.75(1H, s) 7.62(1H, s) 6.50(1H, dt, J=52, 2Hz) 3.10(6H, s) |
| (2) | F | OCF$_2$CFHO | CN | N(CH$_3$)$_2$ | | CDCl$_3$; 7.55(1H, d, J=2Hz) 6.10(1H, dt, J=52, 2Hz) 3.10(6H, s) |
| (3) | Br | OCF$_2$CFHO | CN | N(CH$_3$)$_2$ | | DMSO-d$_6$; 7.80(1H, s) 7.05(1H, dt, J=50, 1Hz) 3.10(6H, s) |
| (4) | H | OCF$_2$CFHO | CSNH$_2$ | N(CH$_3$)$_2$ | 177–179 | CDCl$_3$+DMSO-d$_6$; 9.3(2H, br) 7.6(1H, s) 7.45(1H, s) 6.05(1H, dt, J=54, 3Hz) 3.05(6H, s) |

TABLE 2

Benzimidazole derivatives having the formula (I):

| Compound No. | X | Z | R | Q | Melting point (°C.) | $^1$H-NMR (Internal standard: TMS) Solvent: δ (ppm) |
| --- | --- | --- | --- | --- | --- | --- |
| (5) | F | OCF$_2$CFHO | CSNH$_2$ | N(CH$_3$)$_2$ | | |
| (6) | Br | OCF$_2$CFHO | CSNH$_2$ | N(CH$_3$)$_2$ | | |
| (7) | H | OCF$_2$CF$_2$O | CN | N(CH$_3$)$_2$ | | |
| (8) | F | OCF$_2$CF$_2$O | CN | N(CH$_3$)$_2$ | | |
| (9) | Br | OCF$_2$CF$_2$O | CN | N(CH$_3$)$_2$ | | |
| (10) | F | OCF$_2$CF$_2$O | CSNH$_2$ | N(CH$_3$)$_2$ | | |
| (11) | H | OCF$_2$CH$_2$O | CN | N(CH$_3$)$_2$ | | |
| (12) | F | OCF$_2$CH$_2$O | CN | N(CH$_3$)$_2$ | | |
| (13) | H | OCF$_2$CFClO | CN | N(CH$_3$)$_2$ | | |
| (14) | F | OCF$_2$CFClO | CN | N(CH$_3$)$_2$ | | |

TABLE 3

Benzimidazole derivatives having the formula (I):

| Compound No. | X | Z | R | Q | Melting point (°C.) | $^1$H-NMR (Internal standard: TMS) Solvent: δ (ppm) |
| --- | --- | --- | --- | --- | --- | --- |
| (15) | H | OCF$_2$O | CN | N(CH$_3$)$_2$ | 187–194 decomposed | DMSO-d$_6$; 8.05(1H, s) 8.00(1H, s) 3.05(6H, s) |
| (16) | F | OCF$_2$O | CN | N(CH$_3$)$_2$ | 165–170 | DMSO-d$_6$; 7.90(1H, s) |

TABLE 3-continued

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (17) | Br | OCF$_2$O | CN | N(CH$_3$)$_2$ | decomposed 195–200 | DMSO-d$_6$; 8.00(1H, s) 3.10(6H, s) |
| (18) | H | OCF$_2$O | CSNH$_2$ | N(CH$_3$)$_2$ | decomposed 171–173 | DMSO-d$_6$; 7.75(2H, s) 3.05(6H, s) 3.0(6H, s) |
| (19) | F | OCF$_2$O | CSNH$_2$ | N(CH$_3$)$_2$ | | |
| (20) | Br | OCF$_2$O | CSNH$_2$ | N(CH$_3$)$_2$ | | |

TABLE 4

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (21) | H | OCF$_2$O | CN | N(C$_2$H$_5$)$_2$ | 134–135 | CDCl$_3$; 7.65(1H, s) 7.45(1H, s) 3.55(4H, q, J=7Hz) 1.20(6H, t, J=7Hz) |
| (22) | H | OCF$_2$O | CN | Pyrrolidinyl | 165–170 | CDCl$_3$+DMSO-d$_6$; 7.75(2H, s) 3.40–3.70(4H) 1.80–2.05(4H) |
| (23) | H | OCF$_2$O | CN | Morpholinyl | 204–210 | CDCl$_3$+DMSO-d$_6$; 7.80(2H, s) 3.30–3.90(8H) |
| (24) | Br | OCF$_2$O | CN | N(C$_2$H$_5$)$_2$ | decomposed 174 | CDCl$_3$; 7.55(1H, s) 3.50(4H, q, J=7Hz) 1.15(6H, t, J=7Hz) |

TABLE 5

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (25) | Br | OCF$_2$O | CN | NCH$_3$(C$_2$H$_5$) | 168 | DMSO-d$_6$; 7.85(1H, s) 3.45(2H, q, J=7Hz) 3.00(3H, s) 1.10(3H, t, J=7Hz) |
| (26) | Br | OCF$_2$O | CN | NCH$_3$(CH$_2$Ph) | 136.1 | CDCl$_3$; 7.55(1H, s) 7.10–7.40(5H) 4.50(2H, s) 2.97(3H, s) |
| (27) | Br | OCF$_2$O | CN | Pyrrolidinyl | 186.1 | DMSO-d$_6$; 7.90(1H, s) 3.20–3.70(4H) 1.70–2.00(4H) |
| (28) | Br | OCF$_2$O | CN | Morpholinyl | 206 decomposed | CDCl$_3$; 7.55(1H, s) 3.70–3.90(4H) 3.30–3.50(4H) |

TABLE 5-continued

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|

Note:
Ph represents a phenyl group.

TABLE 6

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (29) | H | CF$_2$CF$_2$O | CN | N(CH$_3$)$_2$ | 132–136 | CDCl$_3$; 8.25(s) 8.05(s) 7.65(s) 7.50(s) These total to 2H, 3.10(6H, s) |
| (30) | H | CF$_2$CF$_2$O | CN | NCH$_3$(C$_2$H$_5$) | | CDCl$_3$; 8.20(s) 8.05(s), 7.63(s) 7.48(s) 3.53(2H, q, J=8Hz) 3.15(3H, s) 1.25(3H, t, J=8Hz) |
| (31) | H | CF$_2$CF$_2$O | CN | NCH$_3$(CH$_2$Ph) | 116.1 | |
| (32) | H | CF$_2$CF$_2$O | CN | Morpholinyl | 151.3 | |
| (33) | H | CF$_2$CF$_2$O | CSNH$_2$ | N(CH$_3$)$_2$ | | CDCl$_3$; 8.35~8.50(1H) 8.20(1H, broad) 7.92(s) 7.88(s) 7.42(s) 7.30(s) These total to 2H, 3.05(6H, s) |
| (34) | Cl | OCF$_2$CFHO | CN | N(CH$_3$)$_2$ | | |
| (35) | Cl | OCF$_2$CF$_2$O | CN | N(CH$_3$)$_2$ | | |
| (36) | Cl | OCF$_2$CFClO | CN | N(CH$_3$)$_2$ | | |

Note:
Ph represents a phenyl group.

TABLE 7

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (37) | Cl | OCF$_2$CH$_2$O | CN | N(CH$_3$)$_2$ | | |
| (38) | H | OCF$_2$CF$_2$O | CSNH$_2$ | N(CH$_3$)$_2$ | | |
| (39) | Cl | OCF$_2$CF$_2$O | CSNH$_2$ | N(CH$_3$)$_2$ | | |
| (40) | Br | OCF$_2$CF$_2$O | CSNH$_2$ | N(CH$_3$)$_2$ | | |
| (41) | Br | OCF$_2$CFClO | CN | N(CH$_3$)$_2$ | | |
| (42) | Br | OCF$_2$CH$_2$O | CN | N(CH$_3$)$_2$ | | |
| (43) | H | OCF$_2$CFClO | CSNH$_2$ | N(CH$_3$)$_2$ | | |
| (44) | F | OCF$_2$CFClO | CSNH$_2$ | N(CH$_3$)$_2$ | | |
| (45) | Cl | OCF$_2$CFClO | CSNH$_2$ | N(CH$_3$)$_2$ | | |
| (46) | Br | OCF$_2$CFClO | CSNH$_2$ | N(CH$_3$)$_2$ | | |

TABLE 8

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (47) | H  | OCF$_2$CH$_2$O | CSNH$_2$ | N(CH$_3$)$_2$ | | |
| (48) | F  | OCF$_2$CH$_2$O | CSNH$_2$ | N(CH$_3$)$_2$ | | |
| (49) | Cl | OCF$_2$CH$_2$O | CSNH$_2$ | N(CH$_3$)$_2$ | | |
| (50) | Br | OCF$_2$CH$_2$O | CSNH$_2$ | N(CH$_3$)$_2$ | | |
| (51) | Cl | OCF$_2$O | CN | N(CH$_3$)$_2$ | | |
| (52) | Cl | OCF$_2$O | CSNH$_2$ | N(CH$_3$)$_2$ | | |
| (53) | H  | CF$_2$OCF$_2$ | CN | N(CH$_3$)$_2$ | 128.5–135 | CDCl$_3$; 8.25(1H, s) 8.15(1H, s) 3.15(6H, s) |
| (54) | H  | CF$_2$OCF$_2$O | CN | N(CH$_3$)$_2$ | | |
| (55) | H  | OCF$_2$O | CN | CH$_3$ | | |
| (56) | H  | CF$_2$CF$_2$O | CN | CH$_3$ | | |
| (57) | H  | OCF$_2$CFHO | CN | CH$_3$ | | |
| (58) | Br | OCF$_2$O | CN | CH$_3$ | | |
| (59) | F  | OCF$_2$O | CN | CH$_3$ | | |

TABLE 9

Benzimidazole derivatives having the formula (I):

| Compound No. | X | Z | R | Q | Melting point (°C.) | $^1$H-NMR (Internal standard: TMS) Solvent: δ (ppm) |
|---|---|---|---|---|---|---|
| (60) | F  | OCF$_2$CFHO | CN | CH$_3$ | | |
| (61) | H  | OCF$_2$O | CN | CH(CH$_3$)$_2$ | 150.3 | |
| (62) | H  | CF$_2$CF$_2$O | CN | CH(CH$_3$)$_2$ | | |
| (63) | H  | OCF$_2$CFHO | CN | CH(CH$_3$)$_2$ | | |
| (64) | Br | OCF$_2$O | CN | CH(CH$_3$)$_2$ | | |
| (65) | F  | OCF$_2$O | CN | CH(CH$_3$)$_2$ | | |
| (66) | F  | OCF$_2$CFHO | CN | CH(CH$_3$)$_2$ | | |
| (67) | H  | OCF$_2$O | CN | NCH$_3$ (CH$_2$C≡CH) | 129–131 | |
| (68) | F  | OCF$_2$O | CN | NCH$_3$ (CH$_2$C≡CH) | | |
| (69) | Br | OCF$_2$O | CN | NCH$_3$ (CH$_2$C≡CH) | | |
| (70) | H  | CF$_2$CF$_2$O | CN | NCH$_3$ (CH$_2$C≡CH) | | |
| (71) | Br | CF$_2$OCF$_2$ | CN | N(CH$_3$)$_2$ | | |
| (72) | Cl | CF$_2$OCF$_2$ | CN | N(CH$_3$)$_2$ | | |
| (73) | H  | CF$_2$OCF$_2$ | CSNH$_2$ | N(CH$_3$)$_2$ | | DMSO-d$_6$; 10.70(1H, broad) 10.25(1H, broad) 8.47(1H, s) 8.35(1H, s) 3.08(6H, s) |
| (74) | H  | CF$_2$OCF$_2$ | CN | N(C$_2$H$_5$)$_2$ | | |
| (75) | H  | CF$_2$OCF$_2$ | CN | NCH$_3$(C$_2$H$_5$) | | |
| (76) | Br | CF$_2$OCF$_2$ | CSNH$_2$ | N(CH$_3$)$_2$ | | |
| (77) | Cl | CF$_2$OCF$_2$ | CSNH$_2$ | N(CH$_3$)$_2$ | | |
| (78) | H  | CF$_2$OCF$_2$ | CN | CH(CH$_3$)$_2$ | | |

Next, production examples for the 2-cyanobenzimidazole compound having the formula (II) will be shown.

Intermediate Production Example 1

3.2 Grams of a 2-(trichloromethyl)benzimidazole compound [compound (101)] of the formula (XI) in which X is H and Z is OCF$_2$CFHO was dissolved in 30 ml of ethanol. The resulting solution was added by drops to 4 ml of a 25% aqueous ammonia at 5° C. After stirring for 1 hour at 5° to 15° C., the reaction solution was poured into an ice/conc. hydrochloric acid mixture and extracted with ethyl acetate. The organic layer was washed with water and dried over anhydrous sodium sulfate. Removing the solvent from the dried layer by distillation gave 2.83 g of a 2-cyanobenzimidazole compound [compound (i)] of the formula (II) in which X is H and Z is OCF$_2$CFHO.

Intermediate Production Example 2

5.3 Grams of a 2-(trichloromethyl)benzimidazole compound [compound (104)] of the formula (XI) in which X is H and Z is OCF$_2$O was suspended in 100 ml of ethanol. The resulting solution was added by drops to 40 ml of a 25% aqueous ammonia at 5° C. After stirring for 1 hour at 5° C. to room temperature, the reaction solution was poured into an ice/conc. hydrochloric acid mixture and extracted with ethyl acetate. The organic layer was washed with water and dried over anhydrous sodium sulfate. Removing the solvent from the dried layer by distillation gave 4.0 g of a 2-cyanobenzimidazole compound [compound (iv)] of the formula (II) in which X is H and Z is $OCF_2O$.

Intermediate Production Example 3

1.0 Gram of a 2-(trichloromethyl)benzimidazole compound [compound (107)] of the formula (XI) in which X is H and Z is $CF_2CF_2O$ was dissolved in 20 ml of ethanol. The resulting solution was added by drops to 5 ml of a 25% aqueous ammonia at 5° C. After stirring for 30 minutes at 5° C., the reaction solution was poured into an ice/conc. hydrochloric acid mixture and extracted with ethyl acetate. The organic layer was washed with water and dried over anhydrous sodium sulfate. Removing the solvent from the dried layer by distillation gave 0.6 g of a 2-cyanobenzimidazole compound [compound (vii)] of the formula (II) in which X is H and Z is $CF_2CF_2O$.

Examples of the compounds which can be produced by the above methods will collectively be shown in Table 10.

TABLE 10

2-Cyanobenzimidazole compound having the formula (II).

| Compound No. | X | Z | $^1$H-NMR (DMSO-$d_6$, TMS) δ (ppm) |
|---|---|---|---|
| (i) | H | $OCF_2CFHO$ | 7.70(2H, s) |
| | | | 6.95(1H, dt, J=52, 2Hz) |
| (ii) | F | $OCF_2CFHO$ | 7.30(1H, d, J=2Hz) |
| | | | 6.15(1H, dt, J=52, 2Hz) |
| (iii) | Br | $OCF_2CFHO$ | 7.65(1H, s) |
| | | | 6.80(1H, dt, J=50, 2Hz) |
| (iv) | H | $OCF_2O$ | 7.70(2H, s) |
| (v) | F | $OCF_2O$ | 7.55(1H, s) |
| (vi) | Br | $OCF_2O$ | 7.75(1H, s) |
| (vii) | H | $CF_2CF_2O$ | 7.95(1H, s) 7.20(1H, s) |
| (viii) | Cl | $OCF_2O$ | |
| (ix) | H | $OCF_2CF_2O$ | |
| (x) | H | $OCF_2CH_2O$ | |
| (xi) | H | $OCF_2CFClO$ | |
| (xii) | H | $CF_2OCF_2$ | 8.50(2H, s) |
| (xiii) | H | $CF_2OCF_2O$ | |

Next, production examples for the 2-(trichloromethyl)benzimidazole compound having the formula (XI) will be shown.

Intermediate Production Example 4

2.5 Grams of an o-phenylenediamine compound [compound (201)] of the formula (XII) in which X is H and Z is $OCF_2CFHO$ was dissolved in 50 ml of acetic acid. 3.8 Grams of methyl trichloroacetoimidate was added thereto at room temperature. The resulting mixture was stirred for 1 hour. The reaction solution was poured into ice water, and precipitated crystals were filtered off. The crystals were dissolved in ethyl acetate. The resulting solution was washed with water and dried over anhydrous sodium sulfate. Removing the solvent from the dried layer by distillation gave 3.2 g of a 2-(trichloromethyl)benzimidazole compound [compound (101)] of the formula (XI) in which X is H and Z is $OCF_2CFHO$.

Intermediate Production Example 5

8.6 Grams of an o-phenylenediamine compound [compound (204)] of the formula (XII) in which X is H and Z is $OCF_2O$ was dissolved in 80 ml of acetic acid. 8.7 Grams of methyl trichloroacetoimidate was added thereto at room temperature. The resulting mixture was stirred for 20 minutes. The reaction solution was poured into ice water, and precipitated crystals were filtered off. The crystals were dissolved in ethyl acetate. The resulting solution was washed with water and dried over anhydrous sodium sulfate. Removing the solvent from the dried layer by distillation gave 5.35 g of a 2-(trichloromethyl)benzimidazole compound [compound (104)] of the formula (XI) in which X is H and Z is $OCF_2O$.

Intermediate Production Example 6

1.0 Gram of an o-phenylenediamine compound [compound (207)] of the formula (XII) in which X is H and Z is $CF_2CF_2O$ was dissolved in 20 ml of acetic acid. 1.4 Grams of methyl trichloroacetoimidate was added thereto at room temperature. The resulting mixture was stirred for 12 hours. The reaction solution was poured into ice water, and precipitated crystals were filtered off. The crystals were dissolved in ethyl acetate. The resulting solution was washed with water and dried over anhydrous sodium sulfate. Removing the solvent from the dried layer by distillation gave 1.0 g of a 2-(trichloromethyl)benzimidazole compound [compound (107)] of the formula (XI) in which X is H and Z is $CF_2CF_2O$.

Examples of the 2-(trichloromethyl)benzimidazole Compounds which can be produced by the above methods will collectively be shown in Table 11.

TABLE 11

2-(Trichloromethyl)benzimidazole compounds having the formula (XI).

| Compound No. | X | Z | $^1$H-NMR (DMSO-$d_6$, TMS) δ (ppm) |
|---|---|---|---|
| (101) | H | $OCF_2CFHO$ | 7.65(2H, s) |
| | | | 7.05(1H, dt, J=52, 1Hz) |
| (102) | F | $OCF_2CFHO$ | 7.20(1H, d, J=1Hz) |
| | | | 6.30(1H, dt, J=52, 2Hz) |
| (103) | Br | $OCF_2CFHO$ | 7.40(1H, s) |
| | | | 6.65(1H, dt, J=52, 1Hz) |
| (104) | H | $OCF_2O$ | 7.60(2H, s) |
| (105) | F | $OCF_2O$ | 7.55(1H, s) |
| (106) | Br | $OCF_2O$ | 7.65(1H, s) |
| (107) | H | $CF_2CF_2O$ | 8.35(1H, s) 7.55(1H, s) |
| (108) | Cl | $OCF_2O$ | |
| (109) | H | $OCF_2CF_2O$ | |
| (110) | H | $OCF_2CH_2O$ | |
| (111) | H | $OCF_2CFClO$ | |
| (112) | H | $CF_2OCF_2$ | 7.90(2H, s)* |
| (113) | H | $CF_2OCF_2O$ | |

*$CDCl_3$ was used as a solvent instead of DMSO-$d_6$.

Next, production examples for the o-phenylenediamine compound having the formula (XII) will be shown.

Intermediate Production Example 7

2.7 Grams of an o-nitroaniline compound [compound (302)] of the formula (XIV) in which X is Br and Z is $OCF_2CFHO$ was dissolved in a mixed solvent of 10 ml of ethyl acetate and 10 ml of acetic acid. The resulting solution was added by drops at 40° C. to a suspension of 2.3 g of iron powders in 3 ml of acetic acid and 30 ml of water. After stirring at 50° to 60° C. for 20 minutes, the reaction mixture was filtered through Celite. The filtrate was extracted with ethyl acetate. The organic layer was washed with an aqueous sodium hydrogencarbonate solution and then with water, and dried over anhydrous sodium sulfate. Removing the solvent from the dried layer by distillation gave 2–44 g of an o-phenylenediamine compound [compound (203)] of the formula (XII) in which X is Br and Z is $OCF_2CFHO$.

Intermediate Production Example 8

2.97 Grams of an o-nitroaniline compound [compound (305)] of the formula (XIV) in which X is Br and Z is $OCF_2O$ was dissolved in a mixed solvent of 10 ml of ethyl acetate and 10 ml of acetic acid. The resulting solution was added by drops at 40° C. to a suspension of 2.4 g of iron powders in 2 ml of acetic acid and 20 ml of water. After stirring at 40° C. to 55° C. for 30 minutes, the reaction mixture was filtered through Celite. The filtrate was extracted with ethyl acetate. The organic layer was washed with an aqueous sodium hydrogencarbonate solution and then with water, and dried over anhydrous sodium sulfate. Removing the solvent from the dried layer by distillation gave 2.52 g of an o-phenylenediamine compound [compound (206)] of the formula (XII) in which X is Br and Z is $OCF_2O$.

Intermediate Production Example 9

1.1 Grams of an o-nitroaniline compound having the formula (XXIV),

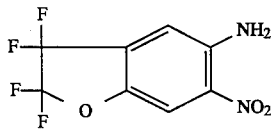
(XXVI)

was dissolved in a mixed solvent of 15 ml of ethyl acetate and 15 ml of acetic acid. The resulting solution was added by drops at 50° C. to a suspension of 1 g of iron powders in 2 ml of acetic acid and 30 ml of water. After stirring at 50° to 60° C. for 10 minutes, the reaction mixture was filtered through Celite. The filtrate was extracted with ethyl acetate. The organic layer was washed with an aqueous sodium hydrogencarbonate solution and then with water, and dried over anhydrous sodium sulfate. Removing the solvent from the dried layer by distillation gave 1.0 g of an o-phenylenediamine compound [compound (207)] of the formula (XII) in which X is H and Z is $CF_2CF_2O$.

The o-phenylenediamine compounds which can be produced by the above methods will be shown in Table 12.

TABLE 12 o-Phenylenediamine compounds having the formula (XII).

| Compound No. | X | Z | $^1$H-NMR (CDCl$_3$, TMS) δ(ppm) |
|---|---|---|---|
| (201) | H | OCF$_2$CFHO | 6.40(2H, s) 5.70(1H, dt, J = 57, 1Hz) 3.30(4H, broad) |
| (202) | F | OCF$_2$CFHO | 6.40(1H, d, J = 2Hz) 5.9(1H, dt, J = 52, 1Hz) 3.55(4H, broad) |
| (203) | Br | OCF$_2$CFHO | 6.45(1H, s) 5.85(1H, dt, J = 53, 2Hz) |
| (204) | H | OCF$_2$O | 6.50(2H, s) 3.30(4,H, broad) |
| (205) | F | OCF$_2$O | 6.28(1H, d, J = 1Hz) 3.35(4H, broad) |
| (206) | Br | OCF$_2$O | 6.45(1H, s) 3.50(4H, broad) |
| (207) | H | CF$_2$CF$_2$O | 6.85(1H, s) 6.30(1H, s) 3.20(4H, broad) |
| (208) | Cl | OCF$_2$O | |
| (209) | H | CF$_2$OCF$_2$ | 6.90(2H, s) 3.85(4H, broad) |

Next, production examples for the o-nitroaniline compound having the formula (XIV) will be shown.

Intermediate Production Example 10

A mixture of 5.07 g of an o-nitroanilide compound [compound (401)] of the formula (XVI) in which X is H, Z is $OCF_2CFHO$ and $R^2$ is $CH_3$, 10 ml of conc. hydrochloric acid and 100 ml of methanol was heated under reflux for 1 hour. The reaction solution was concentrated, poured into ice water and alkalified with potassium carbonate. After extraction with ethyl acetate, the organic layer was washed with water and dried over anhydrous sodium sulfate. Removing the solvent from the dried layer by distillation gave 4.23 g of a compound [compound (301)] of the formula (XIV) in which X is H and Z is $OCF_2CFHO$.

Intermediate Production Example 11

2.67 Grams of the compound (301) was dissolved in 30 ml of acetic acid. To the resulting solution was added by drops 0.3 ml of bromine at room temperature. After addition, stirring was continued for 3 hours at room temperature. The reaction solution was poured into ice water, and precipitated crystals were filtered off. The crystals were dissolved in ethyl acetate. The resulting solution was washed with water and dried over anhydrous sodium sulfate. Removing the solvent from the dried layer by distillation gave 2.7 g of an o-nitroaniline compound [compound (302)] of the formula (XIV) in which X is Br and Z is $OCF_2CFHO$.

Intermediate Production Example 12

A mixture of 7.69 g of an o-nitroanilide compound [compound (402)] of the formula (XVI) in which X is H, Z is $OCF_2O$ and $R^2$ is $CH_3$, 10 ml of conc. hydrochloric acid and 90 ml of methanol was heated under reflux for 1.5 hours. The reaction solution was concentrated, poured into ice water and alkalified with potassium carbonate. After extraction with ethyl acetate, the organic layer was washed with water and dried over anhydrous sodium sulfate. Removing the solvent from the dried layer by distillation gave 4.65 g of a compound [compound (303)] of the formula (XIV) in which X is H and Z is $OCF_2O$.

Intermediate Production Example 13

2.18 Grams of the compound (303) was dissolved in 35 ml of acetic acid. To the resulting solution was added by drops 2 ml of bromine at room temperature. After addition, stirring was continued for 2.5 hours at room temperature to 40° C. The reaction solution was poured into ice water, and precipitated crystals were filtered off. The crystals were dissolved in ethyl acetate. The resulting solution was washed with water and dried over anhydrous sodium sulfate. Removing the solvent from the dried layer by distillation gave 2.50 g of an o-nitroaniline compound [compound (305)] of the formula (XIV) in which X is Br and Z is $OCF_2O$.

Intermediate Production Example 14

A mixture of 1.32 g of an o-nitroacetoanilide compound having the formula (XXV),

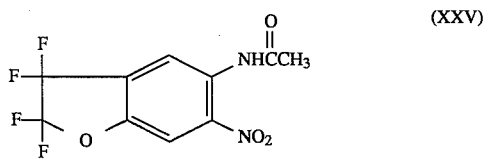
(XXV)

5 ml of conc. hydrochloric acid and 50 ml of methanol was heated under reflux for 80 minutes. The reaction solution was concentrated, poured into ice water and alkalified with potassium carbonate. After extraction with ethyl acetate, the organic layer was washed with water and dried over anhydrous sodium sulfate. Removing the solvent from the dried layer by distillation gave 1.1 g of an o-nitroaniline compound [compound (306)] having the formula (XXIV).

Intermediate Production Example 15

200 Grams of an o-dinitro compound having the formula (XV) in which X is H and Z is $OCF_2O$ was dissolved in 900 ml of N,N-dimethylformamide. The resulting solution was allowed to react at 70° C. for 3 and a half hours while blowing ammonia thereinto. Thereafter, the reaction solution was cooled to room temperature. The cooled solution was filtered through Celite. The filtrate was extracted with diethyl ether. The organic layer was washed with water and dried over anhydrous sodium sulfate. Removing the solvent from the dried layer by distillation gave a residue. The residue was subjected to silica gel column chromatography using chloroform as an eluent to obtain 112.4 g of an o-nitroaniline compound [Compound (303)] having the formula (XIV) in which X is H and Z is $OCF_2O$.

Intermediate Production Example 16

1.60 Grams of an o-chloronitro compound having the formula (XXVI),

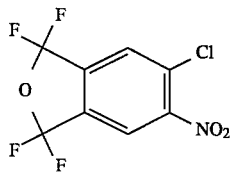

(XXVI)

was dissolved in 30 ml of N,N-dimethylformamide. The resulting solution was allowed to react at 90° C. for 1 hour while blowing ammonia thereinto. Thereafter, the reaction solution was poured into ice water and extracted with ethyl acetate. The organic layer was washed with water. The washed layer was dried over anhydrous sodium sulfate. Removing the solvent from the dried layer by distillation gave a residue. The residue was subjected to silica gel column chromatography using dichloromethane as an eluent to obtain 0.8 g of an o-nitroaniline compound [Compound (308)] having the formula (XIV) in which X is H and Z is $CF_2OCF_2$.

The compounds which can be produced by the above methods will be collectively shown in Table 13.

TABLE 13 o-Nitroaniline compounds having the formula (XIV).

| Compound No. | X | Z | $^1$H-NMR (CDCl$_3$, TMS) &(ppm) |
|---|---|---|---|
| (301) | H | OCF$_2$CFHO | 7.90(1H, s) 7.00(2H, broad) 6.80(1H, s) 6.10(1H, dt, J = 52, 1Hz) |
| (302) | Br | OCF$_2$2CFHO | 8.05(1H, s) 6.65(2H, broad) 5.95(1H, dt, J = 52, 2Hz) |
| (303) | H | OCF$_2$O | 7.85(1H, s) 6.50(1H, s) 6.35(2H, broad) |
| (304) | F | OCF$_2$O | 7.65(1H, d, J = 2Hz) 6.30 (2H, broad) |
| (305) | Br | OCF$_2$O | 7.90(1H, s,) 6.85(2H, broad) |
| (306)* | H | CF$_2$CF$_2$O | 7.80(1H, s) 7.10(1H, s) |

TABLE 13-continued o-Nitroaniline compounds having the formula (XIV).

| Compound No. | X | Z | $^1$H-NMR (CDCl$_3$, TMS) &(ppm) |
|---|---|---|---|
| (307) | Cl | OCF$_2$O | 6.10(2H, broad) |
| (308) | H | CF$_2$OCF$_2$ | 8.40(1H, s) 7.05(1H, s) 6.50(2H, broad) |

Note: *Compound (306) is a compound having the formula (XXIV).

Next, production examples for the o-nitroacetoanilide compound having the formula (XVI) will be shown.

Reference Example 1

4.31 Grams of an anilide compound (compound (501)) of the formula (XVIII) in which X is H, Z is OCF$_2$CFHO and R$^2$ is CH$_3$ was added to 50 ml of conc. sulfuric acid. To the resulting mixture was added by drops a mixture of 3.5 ml of fuming nitric acid and 7 ml of conc. sulfuric acid at −15° C. After addition, stirring was continued for 2 hours at −15° to −10° C. The reaction solution was poured into ice water, and precipitated crystals were filtered off. The crystals were dissolved in ethyl acetate. The resulting solution was washed with water and dried over anhydrous sodium sulfate. A residue was obtained by removing the solvent from the dried layer by distillation. Column chromatographying the residue on silica gel with chloroform as an eluent gave 5.07 g of an o-nitroanilide compound [compound (401)] of the formula (XVI) in which X is H, Z is OCF$_2$CFHO and R$^2$ is CH$_3$.

Reference Example 2

8.9 Grams of an anilide compound [compound (502)] of the formula (XVIII) in which X is H, Z is OCF$_2$O and R$^2$ is CH$_3$ was added to 80 ml of conc. sulfuric acid. To the resulting mixture was added by drops a mixture of 7.5 ml of fuming nitric acid and 15 ml of conc. sulfuric acid at 0° C. After addition, stirring was continued for 0.5 hour at −10° to 0° C. The reaction solution was poured into ice water, and precipitated crystals were filtered off. The crystals were dissolved in ethyl acetate. The resulting solution was washed with water and dried over anhydrous sodium sulfate. A residue was obtained by removing the solvent from the dried layer by distillation. Column chromatographying the residue on silica gel with chloroform as an eluent gave 7.69 g of an o-nitroanilide compound [compound (402)] of the formula (XVI) in which X is H, Z is OCF$_2$O and R$^2$ is CH$_3$.

Reference Example 3

2.69 Grams of an anilide compound having the formula (XXVII),

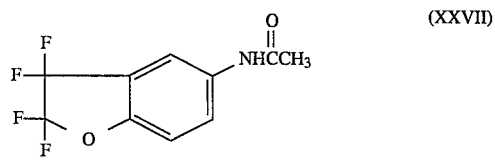

(XXVII)

was added to 50 ml of conc. sulfuric acid. To the resulting mixture was added by drops a mixture of 2.5 ml of fuming nitric acid and 5 ml of conc. sulfuric acid at −10° C. After addition, stirring was continued for 1 hour at −10° to 0° C. The reaction solution was poured into ice water, and precipitated crystals were filtered off. The crystals were dissolved in ethyl acetate. The resulting solution was washed with water and dried over anhydrous sodium sulfate. A residue was obtained by removing the solvent from the dried layer by distillation. Column chromatographying the residue on silica gel with chloroform as an eluent gave 1.32 g of an o-nitroacetoanilide compound [compound (404)] of the formula (XXV).

The compound (404) can also be produced by the method shown in Reference Example 4.

Reference Example 4

7.80 Grams of a compound of the formula (XX) in which Y is Cl and $R^2$ is $CH_3$ was dissolved in 70 ml of N,N-dimethylformamide. 8.0 Grams of copper powders and 0.5 g of 2,2'-bipyridyl were added thereto. Thereafter, stirring was continued at 140° C. for 2 hours. After completion of the reaction, the reaction solution was filtered through Celite. The filtrate was extracted with diethyl ether. The organic layer was washed with water and dried over anhydrous sodium sulfate. A residue was obtained by removing the solvent from the dried layer by distillation. Column chromatographying the residue on silica gel with chloroform as an eluent and recrystallizing it from hexane/ethyl acetate gave 3.06 g of an o-nitroanilide compound [compound (404)] having the formula (XXV).

The compounds produced by the above methods will be collectively shown in Table 14.

TABLE 14

O-Nitroanilide compounds having the formula (XVI).

| Compound No. | X | Z | $R^2$ | $^1$H-NMR ($CDCl_3$, TMS) δ (ppm) |
|---|---|---|---|---|
| (401) | H | $OCF_2CFHO$ | $CH_3$ | 10.35(1H, broad) 8.70(1H, s) 8.00 (1H, s) 6.00(1H, dt, J = 50, 1Hz) 2.30(3H, s) |
| (402) | H | $OCF_2O$ | $CH_3$ | 10.55(1H, broad) 8.70(1H, s) 7.97(1H, s) 2.30(3H, s) |
| (403) | F | $OCF_2O$ | $CH_3$ | 9.60(1H, broad) 7.65(1H, d, J = 2Hz) 2.20(3H, s) |
| (404)* | H | $CF_2CF_2O$ | $CH_3$ | 10.05(1H, broad) 8.75(1H, s, 7.75(1H, s) 2.25(3H, s) |

Note:*Compound (404) is a compound having the formula (XXV).

Next, production examples for the anilide compound having the formula (XVIII) will be shown.

Reference Example 5

4.8 Grams of an aniline compound of the formula (XXI) in which X is H and Z is $OCF_2CFHO$ was dissolved in 50 ml of acetic acid and 2.4 ml of acetic anhydride. The resulting solution was stirred at 70° C. for 10 minutes. The reaction solution was poured into ice water and extracted with ethyl acetate. The organic layer was washed with water and dried over anhydrous sodium sulfate. A residue was obtained by removing the solvent from the dried layer by distillation. Column chromatographying the residue on silica gel with chloroform and ethyl acetate as an eluent gave 4.31 g of an anilide compound [compound (501)] of the formula (XVIII) in which X is H, Z is $OCF_2CFHO$ and $R^2$ is $CH_3$.

Reference Example 6

8.4 Grams of an aniline compound of the formula (XXI) in which X is H and Z is $OCF_2O$ was dissolved in 100 ml of acetic acid and 5 ml of acetic anhydride. The resulting solution was stirred at 60° C. for 5 minutes. The reaction solution was poured into ice water and extracted with ethyl acetate. The organic layer was washed with water and dried over anhydrous sodium sulfate. A residue was obtained by removing the solvent from the dried layer by distillation. Column chromatographying the residue on silica gel with chloroform and ethyl acetate as an eluent gave 8.93 g of an anilide compound [compound (502)] of the formula (XVIII) in which X is H, Z is $OCF_2O$ and $R^2$ is $CH_3$.

The anilide compounds produced by the above methods will collectively be shown in Table 15.

TABLE 15

Anilide compounds having the formula (XVIII).

| Compound No. | X | Z | $R^2$ | $^1$H-NMR (Internal standard: TMS) Solvent: δ (ppm) |
|---|---|---|---|---|
| (501) | H | $OCF_2CFHO$ | $CH_3$ | $CDCl_3$+DMSO–$d_6$; 9.90 (1H, broad) 7.60(1H, d, J = 2Hz) 7.25 (1H, dt, J=8, 2Hz) 7.00(1H, d, J = 8Hz) 6.30 (1H, dt, J = 52, 1Hz) 2.10(3H, s) |
| (502) | H | $OCF_2O$ | $CH_3$ | $CDCl_3$; 9.55(1H, broad) 7.65 (1H, d, J=1Hz) 7.15(1H, dd, J=8, 1Hz) 6.95 (1H, d, J=8Hz) 2.15(3H, s) |
| (503) | F | $OCF_2O$ | $CH_3$ | $CDCl_3$; 7.80(1H, dd, J=8, 8Hz) 7.60(1H, broad) 6.80(1H, dd, J = 8, 1Hz 2.20(3H, s) |

Formulation examples will be shown. In the examples, parts are by weight.

Formulation Example 1

Thoroughly pulverizing and mixing 50 parts of each of the present compounds (1) to (78), 3 parts of calcium lignosulfonate, 2 parts of sodium lauryl sulfate and 45 parts of synthetic hydrated silicon dioxide give a wettable powder of each of the present compounds.

Formulation Example 2

25 Parts of each of the present compounds (1) to (78), 3 parts of polyoxyethylene sorbitan monooleate, 3 parts of CMC and 69 parts of water are mixed. Wet-pulverizing the resulting mixture until the particle size of the active ingredient is reduced to 5 microns or less gives a suspension formulation of each of the present compounds.

Formulation Example 3

Thoroughly pulverizing and mixing 2 parts of each of the present compounds (1) to (78), 88 parts of kaolin clay and 10 parts of talc give a dust of each of the present compounds.

Formulation Example 4

Thoroughly mixing 20 parts of each of the present compounds (1) to (78), 14 parts of polyoxyethylene styrylphenyl ether, 6 parts of calcium dodecylbenzenesulfonate and 60 parts of xylene gives an emulsifiable concentrate of each of the present compounds.

Formulation Example 5

2 Parts of each of the present compounds (1) to (78), 1 part of synthetic hydrated silicon dioxide, 2 parts of calcium lignosulfonate, 30 parts of bentonite and 65 parts of kaolin clay are well pulverized and mixed. The resulting mixture is well kneaded with water, granulated and dried to obtain a granule of each of the present compounds.

Next, the usefulness of the present compound as an agricultural and horticultural fungicide will be shown by test examples. As a control, mancozeb (wettable powder) commonly used as a Phycomycetes-controlling agent was used. The controlling activity in Test Examples 1 to 4 was evaluated in six stages, 5, 4, 3, 2, 1, 0, of the controlling index by macroscopically observing the condition of disease of the test plants, i.e. the degrees of colony and infected area on the leaves, stems, etc., at the time of examination.

5 Infected area is not observed at all.
4 Size of infected area is less than 10% of that in the untreated plot.
3 Size of infected area is less than 30% of that in the untreated plot.
2 Size of infected area is less than 50% of that in the untreated plot.
1 Size of infected area is less than 75% of that in the untreated plot.
0 Size of infected area is 75% or more of that in the untreated plot.

Test Example 1 Controlling test on late blight of tomato (*Phytophthora infestans*) (preventive effect)

Sandy loam was filled in plastic pots, and tomato (var., Ponterosa) was sowed and cultivated for 20 days in a greenhouse to obtain tomato seedlings in the 2nd to 3rd true leaf stage. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were inoculated by spraying the spore suspension of *Phytophthora infestans*. After the inoculation, the seedlings were kept in conditions of 20° C. and high humidity for 1 day and further cultivated for 7 days under lighting. The controlling activity was then examined. The results are shown in Table 16.

TABLE 16

| Compound | Controlling activity | | |
|---|---|---|---|
| | 12.5 | 3.1 | 0.8 ppm |
| (1) | 4 | 2 | 1 |
| (2) | 5 | 4 | 3 |
| (3) | 5 | 4 | 3 |
| (15) | 5 | 4 | 1 |
| (16) | 5 | 5 | 4 |
| (17) | 5 | 4 | 4 |
| (29) | 5 | 4 | 1 |
| (53) | 5 | 5 | 4 |
| Mancozeb | 3 | 0 | 0 |

Test Example 2 Controlling test on late blight of tomato (*Phytophthora infestans*) (curative effect)

Sandy loam was filled in plastic pots, and tomato (var., Ponterosa) was sowed and cultivated for 20 days in a greenhouse to obtain tomato seedlings in the 2nd to 3rd true leaf stage. The seedlings were inoculated by spraying the spore suspension of *phytophthora infestans*. After the inoculation, the seedlings were kept in conditions of 20° C. and high humidity for 1 day. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were cultivated for 7 days under lighting. The controlling activity was then examined. The results are shown in Table 17.

TABLE 17

| Component | Controlling activity | | |
|---|---|---|---|
| | 200 | 50 | 12.5 ppm |
| (1) | 3 | 0 | 0 |
| (2) | 4 | 4 | 1 |
| (15) | 3 | 2 | 0 |
| (16) | 5 | 4 | 3 |
| (17) | 5 | 4 | 3 |
| (29) | 5 | 5 | 3 |
| (53) | 5 | 5 | 3 |
| Mancozeb | 0 | 0 | 0 |

Test Example 3 Controlling test on downy mildew of grape (*Plasmopara viticola*) (preventive effect)

Sandy loam was filled in plastic pots, and grape was sowed and cultivated for 50 days in a greenhouse to obtain grape seedlings in the 3rd to 4th true leaf stage. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were inoculated by spraying the spore suspension of *Plasmopara viticola*. After the inoculation, the seedlings were kept in conditions of 20° C. and high humidity for 1 day and further cultivated for 7 days under lighting. The controlling activity was then examined. The results are shown in Table 18.

TABLE 18

| Compound | Controlling activity | | |
|---|---|---|---|
| | 12.5 | 3.1 | 0.8 ppm |
| (1) | 5 | 1 | 0 |
| (2) | 5 | 3 | 1 |
| (3) | 5 | 4 | 3 |
| (15) | 4 | 1 | 0 |
| (16) | 5 | 4 | 2 |
| (17) | 5 | 5 | 2 |
| (29) | 5 | 5 | 3 |
| (53) | 5 | 5 | 4 |
| Mancozeb | 2 | 0 | 0 |

Test Example 4 Controlling test on downy mildew of grape (*Plasmopara viticola*) (curative effect)

Sandy loam was filled in plastic pots, and grape was sowed and cultivated for 50 days in a greenhouse to obtain grape seedlings in the 3rd to 4th true leaf stage. The seedlings were inoculated by spraying the spore suspension of *Plasmopora viticola*. After the inoculation, the seedlings were kept in conditions of 20° C. and high humidity for 1 day. Thereafter, the wettable powder of the test compound prepared according to Formulation Example 1 was diluted with water to a prescribed concentration and foliar-applied onto the seedlings so that the spray liquor thoroughly adhered to the leaf surface. After the spraying, the seedlings were cultivated for 7 days under lighting. The controlling activity was then examined. The results are shown in Table 19.

TABLE 19

| Compound | Controlling activity | | |
|---|---|---|---|
| | 200 | 50 | 12.5 ppm |
| (1) | 3 | 1 | 0 |
| (2) | 5 | 2 | 1 |
| (15) | 4 | 4 | 0 |
| (16) | 5 | 5 | 4 |
| (17) | 5 | 5 | 4 |
| (29) | 5 | 5 | 3 |
| (53) | 5 | 5 | 5 |
| Mancozeb | 0 | 0 | 0 |

Referential Test Example 1

Controlling test on late blight of tomato (*Phytophthora infestans*) (preventive effect; effect of mixing with various fungicides)

Sandy loam was filled in plastic pots. Tomato (var., Ponterosa) was sowed therein and cultivated for 30 days in a greenhouse to obtain tomato seedlings in the 4th to 5th true leaf stage.

Wettable powders containing one of the present compounds formulated according to Formulation Example 1, various kinds of commercially available fungicide and one of the present compounds and one of the commercially available fungicides were diluted with water to a prescribed concentration. Thereafter, they were foliar-applied onto the seedlings so that the spray liquor thoroughly adhered to the leaf surface. After the spraying, the seedlings were placed for 6 days in a greenhouse. Then, they were inoculated by spraying the spore suspension of *Phytophthora infestans*. After the inoculation, the seedlings were kept in conditions of 20° C. and high humidity for 1 day and further cultivated for 6 days under lighting. For the lowest four true leaves, the following disease indices were determined by their infected areas. Then, the disease severity (%) was defined by the equation 1 below. Further, from the disease severities of the treated and untreated seedlings, the control of disease (%) was defined by the equation 2 below. Table 20 shows the results.

Disease index 5 Outbreak of disease in 90% or more of the true leaves.
Disease index 4 Outbreak of disease in less than 90% of the true leaves.
Disease index 3 Outbreak of disease in less than 60% of the true leaves.
Disease index 2 Outbreak of disease in less than 30% of the true leaves.
Disease index 1 Outbreak of disease in less than 10% of the true leaves.
Disease index 0.5 Outbreak of disease in less than 5% of the true leaves.
Disease index 0 No outbreak of disease Equation 1:

$$\text{Disease severity (\%)} = \frac{\text{Total of the disease indices of 4 true leaves}}{\text{Maximum disease index (5)} \times 4} \times 100$$

Equation 2:

$$\text{Control of disease (\%)} = \frac{\text{Disease severity of untreated seedlings} - \text{disease severity of treated seedlings}}{\text{Disease severity of untreated seedlings}} \times 100$$

TABLE 20

| Test compound | | | |
|---|---|---|---|
| Compound | | Concentration of active ingredient (ppm) | Control of disease (%) |
| (15) | | 25 | 76.2 |
| (17) | | 25 | 92.5 |
| (17) | | 5 | 68.1 |
| Chlorothalonil | (A) | 300 | 85.6 |
| Fluazinam | (B) | 150 | 65.0 |
| Dichlofluanide | (C) | 200 | 84.4 |
| Phosethyl-aluminum | (D) | 400 | 0.0 |
| Captan | (E) | 500 | 76.2 |
| Mancozeb | (F) | 600 | 92.5 |
| Basic cupric chloride | (G) | 600 | 46.2 |
| (A) + (17) | | 300 + 25 | 97.5 |
| (B) + (15) | | 150 + 25 | 85.4 |
| (C) + (15) | | 200 + 25 | 91.2 |
| (D) + (17) | | 400 + 5 | 81.9 |
| (E) + (15) | | 500 + 25 | 95.0 |
| (F) + (17) | | 600 + 25 | 100.0 |
| (G) + (15) | | 600 + 25 | 80.7 |

Referential Test Example 2

Controlling test on downy mildew of cucumber (*Pseudoperonospora cubensis*) (curative and preventive effect; effect of mixing with various fungicides)

Sandy loam was filled in plastic pots. Cucumber (var., Sagamihanjiro) was sowed therein and cultivated for 30 days in a greenhouse to obtain cucumber seedlings in the 4th true leaf stage. Thereafter, the seedlings were inoculated by spraying the spore suspension of *Pseudoperonospora cubensis*. After the inoculation, the seedlings were kept in conditions of 20° C. and high humidity for 1 day. Wettable powders containing one of the present compounds formulated according to Formulation Example 1, various kinds of commercially available fungicide and mixtures of one of the present compounds and one of the commercially available fungicides were diluted with water to a prescribed concentration. Thereafter, they were foliar-applied onto the seedlings so that the spray liquor thoroughly adhered to the leaf surface. After the spraying, the seedlings were placed for 6 days in a greenhouse. Then, they were inoculated again by spraying the spore suspension of *Pseudoperonospora cubensis*. After the re-inoculation, the seedlings were kept in conditions of 20° C. and high humidity for 1 day and further cultivated for 7 days under lighting. For the lowest second, third and fourth true leaves, the disease indices were determined by their infected areas. Then, the disease severity (%)

was defined by the equation 3 below. Further, from the disease severities of the treated and untreated seedlings, the control of disease (%) was defined by the equation 4 below. Table 21 shows the results.

Disease index 10 Outbreak of disease in 90% or more of the true leaves.
Disease index 9 Outbreak of disease in less than 90% of the true leaves.
Disease index 8 Outbreak of disease in less than 80% of the true leaves.
Disease index 7 Outbreak of disease in less than 70% of the true leaves.
Disease index 6 Outbreak of disease in less than 60% of the true leaves.
Disease index 5 Outbreak of disease in less than 50% of the true leaves.
Disease index 4 Outbreak of disease in less than 40% of the true leaves.
Disease index 3 Outbreak of disease in less than 30% of the true leaves.
Disease index 2 outbreak of disease in less than 20% of the true leaves.
Disease index 1 Outbreak of disease in less than 10% of the true leaves.
Disease index 0.5 Outbreak of disease in less than 5% of the true leaves.
Disease index 0 No outbreak of diseases.

TABLE 21

| Test compound | | |
|---|---|---|
| Compound | Concentration of active ingredient (ppm) | Control of disease |
| (15) | 200 | 53.5 |
| (15) | 100 | 21.1 |
| (17) | 200 | 99.2 |
| (17) | 100 | 96.5 |
| N-[cyano(2'-furyl)-methyl]-2,4-dimethyl-thiazole-5-carboxy-amide (H) | 200 | 86.0 |
|  | 100 | 75.5 |
| Cymoxanil (I) | 200 | 76.3 |
| Cymoxanil | 100 | 42.1 |
| Metalaxyl (J) | 200 | 92.1 |
|  | 100 | 91.3 |
| (H) + (15) | 100 + 100 | 100.0 |
| (H) + (15) | 50 + 50 | 100.0 |
| (H) + (17) | 100 + 100 | 100.0 |
| (H) + (17) | 50 + 50 | 100.0 |
| (I) + (15) | 100 + 100 | 98.2 |
| (I) + (17) | 100 + 100 | 100.0 |
| (I) + (17) | 50 + 50 | 100.0 |
| (J) + (15) | 100 + 100 | 98.2 |
| (J) + (17) | 100 + 100 | 100.0 |
| (J) + (17) | 50 + 50 | 100.0 |

Equation 3:

$$\text{Disease severity (\%)} = \frac{\text{Total of the disease indices of 3 true leaves}}{\text{Maximum disease index (10)} \times 3} \times 100$$

Equation 4:

$$\text{Control of disease (\%)} = \frac{\text{Disease severity of untreated seedlings} - \text{disease severity of treated seedlings}}{\text{Disease severity of untreated seedlings}} \times 100$$

The present compound has excellent controlling effect on various plant diseases, particularly plant diseases caused by Phycomycetes such as downy mildew, late blight and the like, and further gives no such phytotoxicity as would become a problem to crops. Consequently, the present compound can be applied to various uses as an active ingredient for agricultural and horticultural fungicides.

What is claimed is:

1. A benzimidazole derivative having the formula,

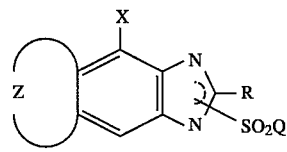

wherein R is cyano or thiocarbamoyl; Q is lower alkyl or a group represented by the formula $NQ^1Q^2$, in which $Q^1$ and $Q^2$ are independently lower alkyl, lower alkyl substituted with phenyl, lower alkenyl or lower alkynyl, or when taken together at their ends, they form a lower alkylene ring or $-CH_2CH_2OCH_2CH_2-$ or $-CH_2CH_2SCH_2CH_2-$; X is hydrogen or halogen; Z is $-CF_2OCF_2-$.

2. A benzimidazole derivative according to claim 1 wherein Q is ethyl.

3. A benzimidazole derivative according to claim 1, wherein Q is dimethylamino.

4. A compound of the formula,

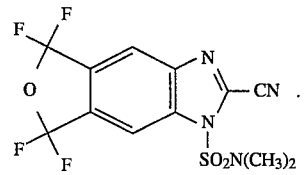

5. An agricultural and horticultural fungicide composition which comprises as an active ingredient an agriculturally and horticulturally effective amount of a benzimidazole derivative according to claim 1 and an inert carrier.

6. A method for controlling plant diseases which comprises applying a fungicidally effective amount of a compound according to claim 1.

* * * * *